United States Patent [19]
Schnaibel et al.

[11] Patent Number: 5,669,219
[45] Date of Patent: Sep. 23, 1997

[54] METHOD AND DEVICE FOR MONITORING A HEATING DEVICE OF A SENSOR MOUNTED IN THE EXHAUST SYSTEM OF AN INTERNAL COMBUSTION ENGINE

[75] Inventors: Eberhard Schnaibel, Hemmingen; Erich Junginger, Stuttgart; Erich Schneider, Kirchheim, all of Germany

[73] Assignee: Robert Bosch GmbH, Stuttgart, Germany

[21] Appl. No.: 468,862

[22] Filed: Jun. 6, 1995

[30] Foreign Application Priority Data

Sep. 21, 1994 [DE] Germany ............... 44 33 632.2

[51] Int. Cl.⁶ .................................................. F01N 3/28
[52] U.S. Cl. ................ 60/274; 60/276; 60/277; 123/697
[58] Field of Search ............... 60/276, 277, 274; 123/697, 688, 690

[56] References Cited

U.S. PATENT DOCUMENTS

| | | |
|---|---|---|
| 4,724,815 | 2/1988 | Mieno ............................ 123/697 |
| 4,928,518 | 5/1990 | Tamura . | 
| 4,958,611 | 9/1990 | Uchinami ........................ 123/697 |
| 5,090,387 | 2/1992 | Mayer et al. . |
| 5,167,120 | 12/1992 | Junginger ....................... 123/697 |
| 5,218,946 | 6/1993 | Wild ............................... 123/697 |
| 5,228,426 | 7/1993 | Pursifull et al. . |
| 5,245,979 | 9/1993 | Pursifull ......................... 123/697 |
| 5,285,762 | 2/1994 | Werner ........................... 123/697 |
| 5,331,808 | 7/1994 | Koike ............................... 60/277 |

FOREIGN PATENT DOCUMENTS 39 28 709  3/1991  Germany .

*Primary Examiner*—Douglas Hart

[57] ABSTRACT

A method and device for monitoring a heating device of a sensor mounted in the exhaust system of an internal combustion engine. In assessing the working order of the heating device, use is made of the fact that a sensor heated by a heating element heats up more strongly than an unheated sensor, and that it is possible to establish, with the aid of the signals output by the sensor, whether the sensor has exceeded its minimum operating temperature. The temperature of the sensor is simulated as a function of internal combustion engine operating characteristics. The working order of the heating device can be assessed with the aid of the simulated temperature and the information as to whether the minimum operating temperature is exceeded.

11 Claims, 4 Drawing Sheets

METHOD AND DEVICE FOR MONITORING A HEATING DEVICE OF A SENSOR MOUNTED IN THE EXHAUST SYSTEM OF AN INTERNAL COMBUSTION ENGINE

FIELD OF THE INVENTION

The present invention relates to a method and device for monitoring a heating device of a sensor mounted in the exhaust system of an internal combustion engine.

BACKGROUND INFORMATION

In modern motor vehicles, there is usually arranged in the exhaust system of the internal combustion engine at least one sensor which is not operationally ready until a specific temperature has been exceeded. This can be, for example, a lambda probe. The sensor is heated by the hot exhaust gases passing by. In order to achieve the minimum operating temperature of the sensor as quickly as possible after the internal combustion engine has been started, and also to ensure it in operating ranges in which the heating effect of the exhaust gases alone is not sufficient for this purpose, it is customary to provide the sensor with an electric heating device. In the event of a fault in the heating device, the working order of the sensor can be greatly impaired.

For this reason, it is usual to provide measures for detecting a fault which may possibly occur. U.S. Pat. No. 5,090,387 (corresponding to German Patent Application No. DE 39 28 709) describes a method and a device for checking the working order of a heating device for an exhaust-gas probe and the supply leads thereof. In the known method, the operational readiness of the exhaust-gas probe is detected after the heating device has been switched on at two successive prescribed times, t1 and t2. If the operational readiness is lacking after expiry of time t1 and, by contrast, is present after expiry of time t2, it is concluded that the heating device has failed. The known functional diagnosis is based on the assumption that the exhaust-gas probe reaches its minimum operating temperature more quickly when the heating device is switched on and in working order than in the case of being heated solely by the exhaust gases.

The object of the present invention is to guarantee a reliable monitoring of the heating device of a sensor arranged in the exhaust system of an internal combustion engine.

SUMMARY OF THE INVENTION

The present invention has the advantage that it renders possible a reliable monitoring of the heating device of a sensor mounted in the exhaust system of an internal combustion engine.

In the method according to the present invention, a first signal is formed which specifies the operational readiness of the sensor. Furthermore, a second signal is formed which specifies the temperature of the sensor. The heating device is assessed as being in working order when the first signal specifies that the sensor is operationally ready and the second signal is within a prescribable first range. The heating device is assessed as not being in working order when the first signal specifies that the sensor is operationally ready and the second signal is within a prescribable second range. When the first signal specifies that the sensor is operationally ready and the second signal is within a prescribable third range, no statement is made on the working order of the heating device.

It is particularly advantageous in this case that both the first and the second signals are available without a large outlay. The first signal is determined from the output signals of the sensor. The second signal is formed as a function of operating characteristics of the internal combustion engine by providing a fundamental signal with at least one correction. The fundamental signal is determined as a function of a signal which specifies the air flow rate through the internal combustion engine. The correction represents the temperature influence of the wall of the exhaust system or/and the dynamic response of the temperature of the sensor. In the case of a sensor arranged downstream of a catalytic converter, the correction further represents the temperature influence of the catalytic converter.

DETAILED DESCRIPTION OF THE INVENTION

Figure 1:
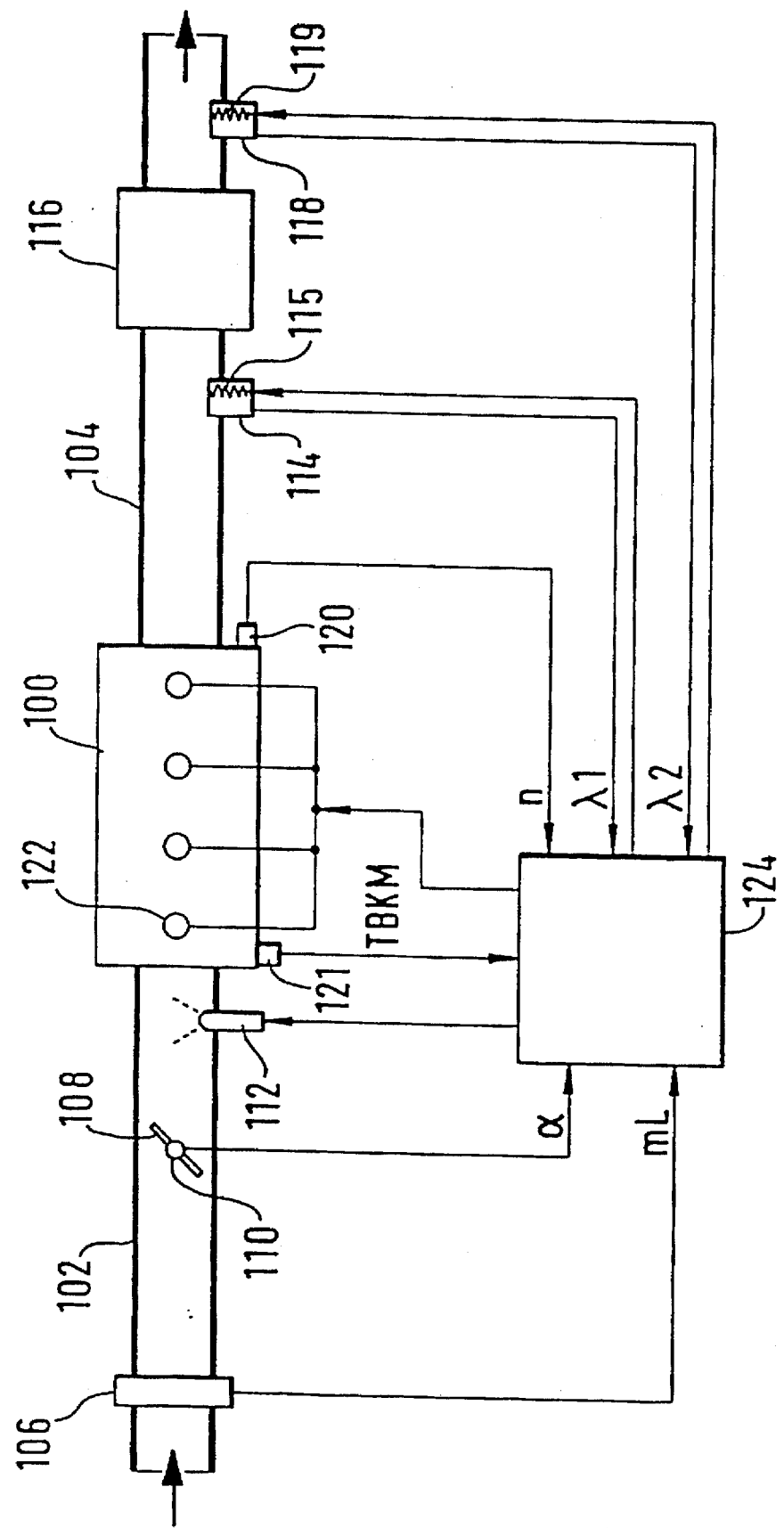
FIG. 1 shows a block diagram of an internal combustion engine and exhaust system in which the method according to the present invention can be used.

FIG. 1 shows a schematic representation of the technical field in which the present invention can be used. An internal combustion engine 100 is fed an air/fuel mixture via an intake tract 102, and the exhaust gases are discharged into an exhaust duct 104. Seen in the direction of flow of the intake air are an air-flow sensor or air mass meter 106, for example a hot film air mass meter, a throttle valve 108 having a sensor 110 for detecting the opening angle of the throttle valve 108, and at least one injection nozzle 112 arranged in the intake tract 102.

Seen in the direction of flow of the exhaust gas, a first oxygen sensor 114, a catalytic converter 116, and a second oxygen sensor 118 are arranged in the exhaust duct 104. The oxygen sensors 114 and 118 can be electrically heated by means of heating devices 115 and 119, respectively. A speed sensor 120 and a temperature sensor 121 are fitted into the internal combustion engine 100.

Furthermore, the internal combustion engine 100 has, for example, four spark plugs 122 for igniting the air/fuel mixture in the cylinders. The output signals mL of the air-flow sensor or air mass meter 106, $\alpha$ of the sensor 110 for detecting the opening angle of the throttle valve 108, $\lambda 1$ of the first oxygen sensor 114, $\lambda 2$ of the second oxygen sensor 118, n of the speed sensor 120, and TBKM of the temperature sensor 121 are fed to a central control unit 124 via corresponding connecting lines. The control unit 124 evaluates the sensor signals and drives the injection nozzle or the injection nozzles 112 and the spark plugs 122 via further connecting lines and heating devices 115 and 119. Furthermore, the control unit 124 carries out the method according to the present invention.

Figure 2:
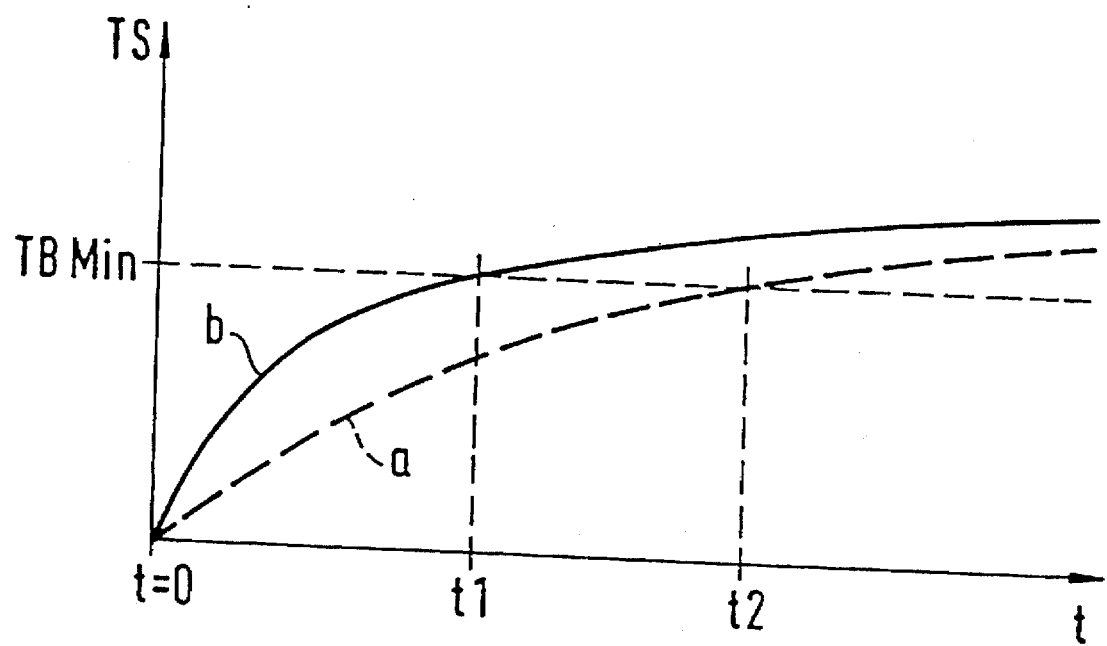
FIG. 2 shows a diagram of a typical characteristic of the sensor temperature after starting the internal combustion engine for the case of a heating device which is in full working order and for the case of a heating device which is completely out of working order.

FIG. 2 shows a diagram of, in each case, a typical characteristic of the sensor temperature TS of the oxygen sensor 114 or 118 after starting the internal combustion engine 100 for the case of a heating device 115 or 119 which is in full working order. Plotted on the abscissa is the time t from the starting of the internal combustion engine 100, and on the ordinate is the sensor temperature TS. For the purposes of simplification, the present invention is explained below by way of example with the aid of the oxygen sensor 114 and the heating device 115. The present invention can, however, likewise be used in conjunction with the oxygen sensor 118 and the heating device 119.

The dashed curve a in FIG. 2 reproduces the temperature characteristic without heating device 115, that is to say, for the case of a heating device 115 which is completely out of working order. The continuous curve b reproduces the temperature characteristic with heating device 115, that is to say, for a heating device 115 which is in full working order. The curves a and b start at the same sensor temperature TS at time t=0, at which time the internal combustion engine 100 is started. From this time, t=0, the oxygen sensor 114 is heated by hot exhaust gases which pass by it, that is to say the sensor temperature TS rises. As a result of this, the curves a and b rise from time t=0.

Since when the internal combustion engine 100 is started, the heating device 115 of the oxygen sensor 114 is additionally activated in the case of curve b, the oxygen sensor 114 is additionally electrically heated, with the result that the sensor temperature TS rises quickly. In the case of curve a, the electric heating is absent, and as a result the sensor temperature TS rises slowly, that is to say, the curve a runs below the curve b. After a time t1, the curve b has reached the minimum operating temperature, TBMin, of the oxygen sensor 114. At this time t1, the curve a is still substantially below the minimum operating temperature TBMin. That is to say, at time t1 the oxygen sensor 114 is already operationally ready if it is additionally heated electrically from time t=0 using the heating device 115, while without additional electric heating the oxygen sensor 114 is still not operationally ready at time t1.

At time t2, the curve a also then reaches the minimum operating temperature TBMin. The oxygen sensor 114 without electric heating is consequently operationally ready from time t2. It may thus be stated overall that the oxygen sensor 114 reaches its minimum operating temperature TBM in more quickly when it is additionally heated electrically. A faulty heating device 115 lengthens the time interval until the minimum operating temperature TBMin is reached. The temperature characteristics represented in FIG. 2 relate to a very specific load profile of the internal combustion engine 100. A different load profile also entails somewhat different temperature characteristics. As explained in closer detail further below, the method according to the present invention can be applied for different load profiles as long as the load remains below a threshold value.

Figure 3:
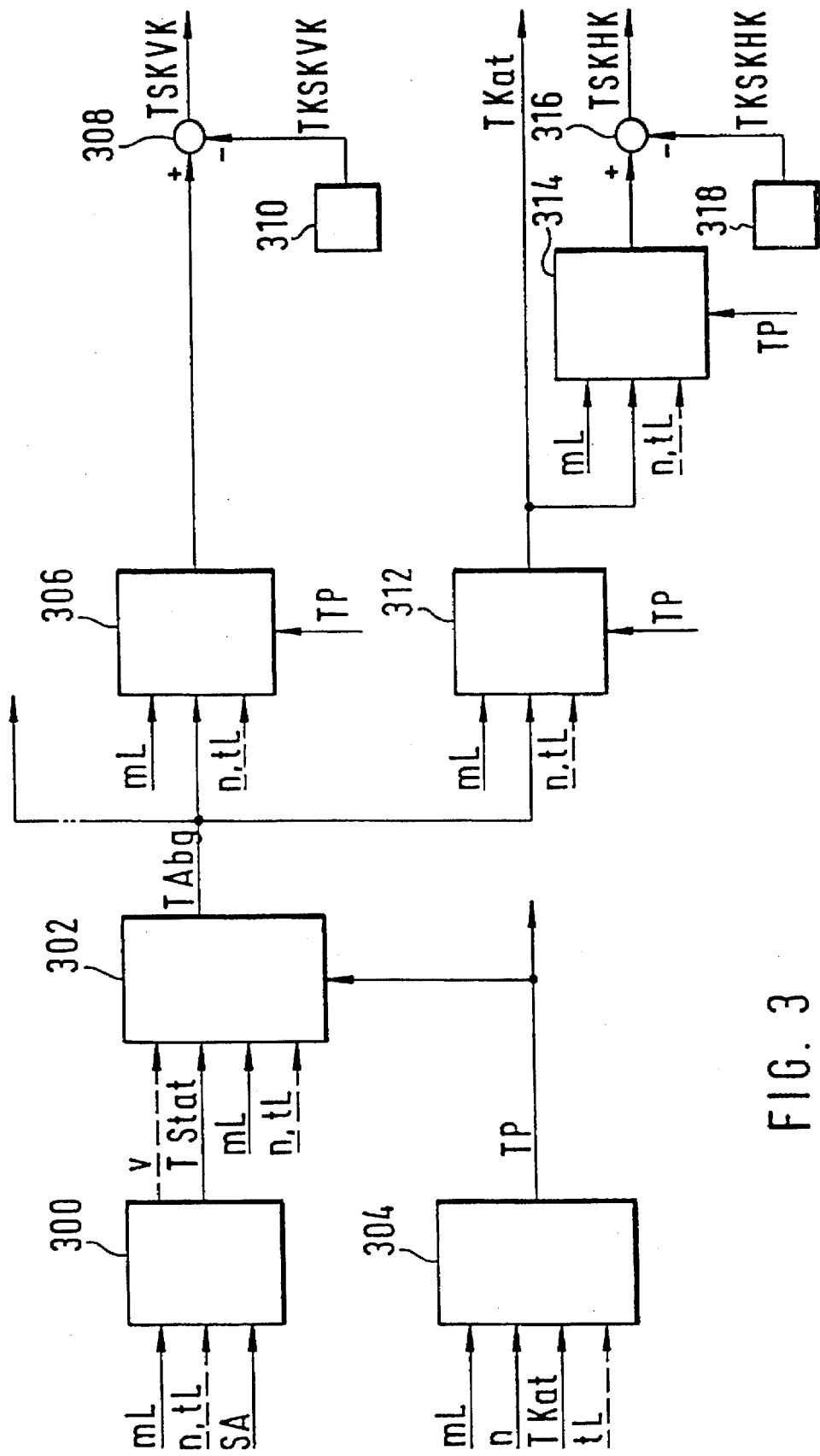
FIG. 3 shows a block diagram of a device according to the present invention for simulating the sensor temperature.

FIG. 3 shows a block diagram of a device according to the present invention by means of which the temperature of the oxygen sensor 114 and the temperature of the oxygen sensor 118 can be simulated. The exemplary embodiment in accordance with FIG. 3 is designed for the case in which the oxygen sensors 114 and 118 are heated only by the exhaust gas, that is to say, in which the heating devices 115 and 119 are out of operation. The simulation of the sensor temperatures is performed as a function of operating characteristics, of which initially a signal TStat for a steady-state exhaust-gas temperature is first determined. This signal TStat is subsequently subjected to a series of further processing steps in order to take account of influences of, for example, the non-steady-state operation of the internal combustion engine 100, of cooling during transport through the exhaust system, of condensed water which may be present, of the warm-up response of the oxygen sensors 114 and 118, and of the catalytic converter 116. Details on this are described below.

A signal mL, which specifies the mixture flow rate through the internal combustion engine 100, is fed into a block 300. Instead of the signal mL, it is also possible to use a signal n for the speed and a signal tL for the load on the internal combustion engine. Furthermore, a signal SA which specifies whether the internal combustion engine 100 is coasting is fed into the block 300. The signal SA can be determined in a known way from the signal a for the throttle valve angle and from the signal n for the speed. The block 300 determines from the input variables the signal TStat for the steady-state exhaust-gas temperature. The operation of block 300 is described, for example, in German Application No. DE 43 38 342.

The output of the block 300 is connected to an input of a block 302. Present at further inputs of the block 302 are a signal v for the vehicle speed and the signal mL or the signals n and tL. Present at a further input is a signal TP which specifies whether condensed water is present in the exhaust system of the internal combustion engine 100. The signal TP is output by a block 304 into which the signal mL or the signal tL, the signal n and a signal TKat for the temperature of the catalytic converter 116 are fed. Details on the determination of the signal TKat are described below. The operation of block 304 likewise already has been described, for example, in German Patent Application No. DE 43 38 342. The block 302 determines from its input signals a signal TAbg for the exhaust-gas temperature and provides this signal at its output. The signal TAbg represents the exhaust-gas temperature immediately upstream of the catalytic converter 116.

The output of the block 302 is connected to an input of a block 306. Present at further inputs of the block 306 are the signal mL, or the signals n and tL, and the signal TP. The block 306 forms the temperature of the oxygen sensor 114 as a function of the above named input variables, that is to say, it determines from data on the exhaust-gas temperature, the mixture flow rate, and the presence of condensed water, a signal which specifies the temperature of the oxygen sensor 114, and provides this signal at its output. The block 306 can be realized as a filter—for example, as a low-pass filter—and effect filtering of the signal TAbg, the filter effect being a function of the signal mL. It is possible to activate in the filter, as a function of the signal TP, a limiting function which limits the output signal to a prescribable value.

The output of the block 306 is connected to a first input of a logic point 308, whose second input is connected to the output of a block 310. The aim is to use the logic point 308 and the block 310 to take account of the cooling effect which the tube wall of the exhaust-gas duct 104 generally exerts on the oxygen sensor 114. In a very simple embodiment, the block 310 is designed as a read-only memory in which a fixed temperature value is stored, for example 50° C. The block 310 outputs a signal TKSKVK which corresponds to the stored value and is subtracted at the logic point 308 from the signal output by the block 306. The result of this arithmetic operation is provided as the signal TSKVK at the output of the logic point 308 and specifies the simulated temperature of the oxygen sensor 114 which is required for the method according to the present invention.

Further functional groups, by means of which it is possible to simulate the temperature of the oxygen sensor 118 which is arranged downstream of the catalytic converter 116, are provided in FIG. 3. For this purpose, an input of a block 312 is connected to the output of the block 302, that is to say the signal TAbg for the exhaust-gas temperature is fed into the block 312. Present at further inputs of the block 312 are the signal mL, or the signals n and tL, and the signal TP. The block 312 determines a signal TKat for the temperature of the catalytic converter 116 from the input variables. The block 312 can be designed in principle in exactly the same way as the block 306, it being required only that a different dimensioning be undertaken in order, for example, to take account of the strongly differing thermal masses of the oxygen sensor 114 and the catalytic converter 116.

The output of the block 312 is connected to an input of a block 314. The signal mL, or the signals n and tL, and the signal TP are present at further inputs of the block 314. The block 314 determines a signal for the temperature of the oxygen sensor 118 from the input variables. The design of the block 314 again can be identical with the design of the block 306, and if the oxygen sensors 114 and 118 are the same, the dimensioning of the block 314 also can be identical with that of the block 306.

The output of the block 314 is connected to a first input of a logic point 316 whose second input is connected to the output of a block 318. The block 318 and the logic point 316 correspond in their method of functioning to the block 310 and the logic point 308, that is to say, they correct the signal output by the block 314 by a value which corresponds to the cooling by the tube wall of the exhaust-gas duct 104. A signal TKSKHK is output by the block 318 for this purpose. The logic point 316 outputs a signal TSKHK which represents the temperature of the oxygen sensor 118. This signal is required in case the method according to the present invention is to be used to monitor the oxygen sensor 118 which is arranged downstream of the catalytic converter 116.

Figure 4:
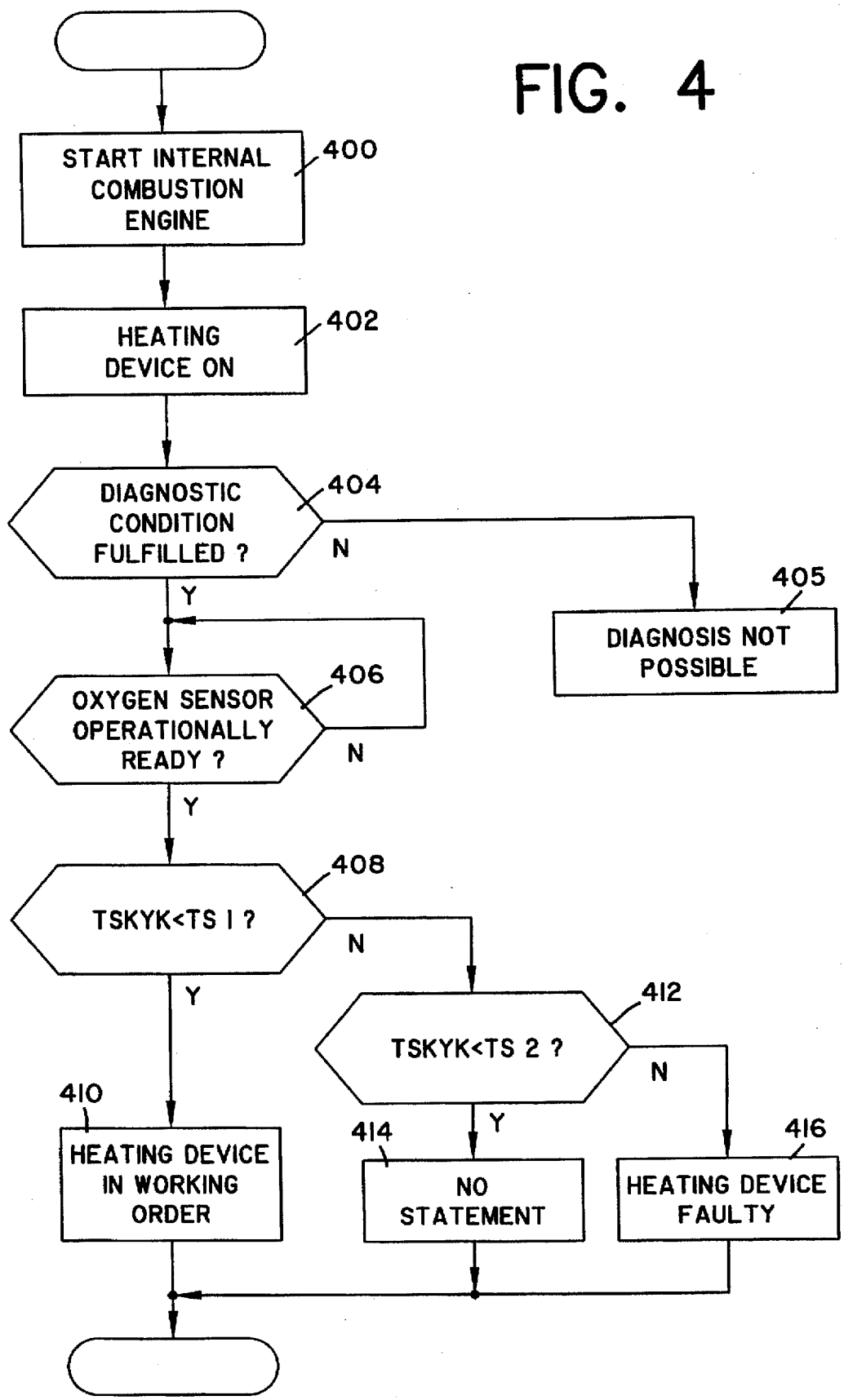
FIG. 4 shows a flow diagram of the method according to the present invention.

FIG. 4 shows a flow diagram of the method according to the present invention. The method represented in FIG. 4 can, for example, be activated after starting the internal combustion engine 100. It starts with a step 400, in which the internal combustion engine 100 is started. The step 400 is followed by a step 402, in which the heating device 115 of the oxygen sensor 114 or the heating device 119 of the oxygen sensor 118 is switched on. An interrogation 404 follows the step 402. It is checked in the interrogation 404 whether a diagnostic condition is fulfilled. The diagnostic condition is fulfilled when the air mass flow is below a prescribable value, the temperature of the internal combustion engine is below a prescribable value, the battery voltage is above a prescribable value, and the oxygen sensor 114 or 118 is not faulty.

The interrogation 404 is followed by a step 405 if the interrogation 404 is answered no, that is to say, the diagnostic condition is not fulfilled. It is established in step 405 that a diagnosis of the heating device 115 or 119 is not possible under the given operating conditions, and the pass through the flow diagram is thereby terminated. If the interrogation 404, by contrast, is answered yes, an interrogation 406 follows. The question is posed in the interrogation 406 whether the oxygen sensor 114 or 119 is operationally ready. The operational readiness can be assessed with the aid of the signals output by the oxygen sensor 114 or 118. If these signals exceed a threshold value, operational readiness obtains. If no operational readiness obtains, the interrogation 406 is carried out anew.

If operational readiness obtains, an interrogation 408 follows in which the question is posed whether the signal TSKVK for the temperature of the oxygen sensor 114, or the signal TSKHK for the temperature of the oxygen sensor 118, is smaller than a threshold value TS1. The signals TSVK and TSHK are determined using the device according to the present invention represented in FIG. 3, and respectively relate to the sensor temperature without electric heating. If the interrogation 408 is fulfilled, that is to say, if the signal TSKVK or the signal TSKHK is smaller than the threshold value TS1, the interrogation 408 is followed by a step 410 in which it is concluded that the heating device 115 or 119 is in working order. This conclusion is to be explained with the aid of the diagram represented in FIG. 1.

In order to reach the interrogation 408, it would be necessary, in advance in the interrogation 406, to establish an operational readiness of the oxygen sensor 114 or 118, that is to say, that the electrically heated oxygen sensor 114 or 118 has exceeded the minimum operating temperature, represented in FIG. 2 as TBMin. The continuous curve b in FIG. 2 represents the temperature of the oxygen sensor 114 or 118 with an activated electric heating device 115 or 119. In order to be able to conclude reliably that the heating device is in working order, the dashed curve a for the temperature characteristic of the oxygen sensor 114 or 118 without additional electric heating must be clearly below the curve b. This is checked by means of the interrogation 408.

There, the temperature TSKVK or TSKHK simulated for an oxygen sensor 114 or 118 without additional electric heating is compared with a threshold value TS1. The threshold value TS1 is smaller than TBMin, so that the question is posed in the interrogation 408 whether the temperature of the oxygen sensor 114 or 118 without additional electric heating is clearly smaller than TBMin. If this is the case, a clear rise in temperature due to the effect of the heating device 115 or 119 can be established, and it can therefore be concluded that the heating device 115 or 119 is in proper working order. If, by contrast, this is not the case, that is to say, the interrogation 408 is not fulfilled, it is to be checked whether it is possible to conclude with sufficient reliability that the heating device 115 or 119 is completely or partially in working order, or whether no unambiguous statement is possible under the given conditions.

In this case, an interrogation 412 follows the interrogation 408 for this purpose. The question is posed in the interrogation 412 as to whether the signal TSKVK or TSKHK for the temperature which the oxygen sensor 114 or 118 would have without electric heating by the heating device 115 or 119 is below a threshold value TS2. The threshold value TS2 is larger than the threshold value TS1. If the interrogation 412 is fulfilled, the signal TSKVK or TSKHK is located in the interval between TS1 and TS2. A reliable statement on the functional state of the heating device 115 or 119 is not possible in this region, and the interrogation 412 is followed by an interrogation 414 in which it is concluded that it is not possible to make a reliable statement on the functional state of the heating device 115 or 119. The step 414 terminates the pass through the flow diagram. If, by contrast, the interrogation 412 is not fulfilled, that is to say, if the signal TSKVK or TSRHK is not smaller than the threshold value TS2, the step 412 is followed by a step 416 in which it is concluded that the heating device 115 or 119 is faulty. Furthermore, in the step 416 a suitable warning device can be activated and an entry can be made in a fault memory. The pass through the flow diagram is terminated by the step 416.

As an alternative to the previous description, the device of FIG. 3 also can be modified in such a way that it simulates the temperature of the oxygen sensor 114 or/and of the oxygen sensor 118 while taking account of the rise in temperature caused by the electric heating device 115 or/and 119. The checking of the working order is to be correspondingly tuned thereto. For example, it is possible to wait until the simulated sensor temperature exceeds the minimum operating temperature by a prescribable value, and then to pose the question of whether operational readiness of the oxygen sensor 114 or 118 obtains. If operational readiness obtains, the heating device 115 or 119 is assessed as being in working order. If operation readiness does not obtain, the heating device 115 or 119 is assessed as being not in working order.

Still further embodiments of the present invention are possible. The essential point in this is that the working order of the heating device 115 or 119 is assessed as a function of the established operational readiness of the oxygen sensor 114 or 118, from which it can be derived that the minimum operating temperature is reached, and of the temperature, simulated from operating characteristics, of the oxygen sensor 114 or 118.

What is claimed is:

1. A method for monitoring a heating device of a sensor mounted in an exhaust system of an internal combustion engine, comprising the steps of:

forming a first signal indicative of an operational readiness of the sensor;

forming a second signal indicative of a temperature of the sensor; and determining an operational state of the heating device as a function of the first signal and the second signal, the operational state including one of a working order and a non-working order, the heating device being in the working order when the first signal indicates the operational readiness of the sensor and the second signal has a value within a predetermined first range.

2. The method according to claim 1, wherein the heating device is in the non-working order when the first signal indicates the operational readiness of the sensor and the second signal is within a predetermined second range.

3. A method for monitoring a heating device of a sensor mounted in an exhaust system of an internal combustion engine, comprising the steps of:

forming a first signal indicative of an operational readiness of the sensor;

forming a second signal indicative of a temperature of the sensor; and determining an operational state of the heating device as a function of the first signal and the second signal, the operational state including one of a working order and a non-working order, and a no-statement order, the heating device being in the working order when the first signal indicates the operational readiness of the sensor and the second signal has a value within a predetermined first range, the no-statement order existing when the first signal indicates the operational readiness of the sensor and the second signal is within a predetermined third range.

4. The method according to claim 1, wherein the step of forming the second signal includes forming the second signal signal as a function of at least one operating characteristic of the internal combustion engine.

5. A method for monitoring a heating device of a sensor mounted in an exhaust system of an internal combustion engine, comprising the steps of:

forming a first signal indicative of an operational readiness of the sensor;

forming a second signal indicative of a temperature of the sensor;

determining an operational state of the heating device as a function of the first signal and the second signal, the operational state including one of a working order and a non-working order, the heating device being in the working order when the first signal indicates the operational readiness of the sensor and the second signal has a value within a predetermined first range; and forming a fundamental signal as a function of an air flow rate signal through the internal combustion engine, wherein the step of forming the second signal includes forming the second signal as a function of the fundamental signal and at least one correction signal.

6. The method according to claim 5, wherein the at least one correction signal is determined as a function of an influence of temperature on a wall of the exhaust system.

7. The method according to claim 5, wherein the at least one correction signal is determined as a function of a dynamic response of the temperature of the sensor.

8. The method according to claim 5, wherein the exhaust system includes a catalytic converter, the sensor being arranged downstream of the catalytic converter, the at least one correction signal being determined as a function of a temperature influence of the catalytic converter.

9. A device for monitoring a heating device of a sensor mounted in an exhaust system of an internal combustion engine, comprising a control unit coupled to the sensor, the control unit forming a first signal indicative of an operational readiness of the sensor, forming a second signal indicative of a temperature of the sensor, and determining an operational state of the heating device as a function of the first signal and the second signal, the operational state including one of a working order and a non-working order, the heating device being in the working order when the first signal indicates the operational readiness of the sensor and the second signal is within a predetermined first range.

10. A device for monitoring a heating device of a sensor mounted in an exhaust system of an internal combustion engine, comprising a control unit coupled to the sensor, the control unit forming a first signal indicative of an operational readiness of the sensor, forming a second signal indicative of a temperature of the sensor, and determining an operational state of the heating device as a function of the first signal and the second signal, the operational state including one of a working order and a non-working order, and a no-statement order, the heating device being in the working order when the first signal indicates the operational readiness of the sensor and the second signal is within a predetermined first range, the no-statement order existing when the first signal indicates the operational readiness of the sensor and the second signal is within a predetermined third range.

11. A device for monitoring a heating device of a sensor mounted in an exhaust system of an internal combustion engine, comprising a control unit coupled to the sensor, the control unit forming a first signal indicative of an operational readiness of the sensor, forming a second signal indicative of a temperature of the sensor, determining an operational state of the heating device as a function of the first signal and the second signal, the operational state including one of a working order and a non-working order, the heating device being in the working order when the first signal indicates the operational readiness of the sensor and the second signal is within a predetermined first range, and forming a fundamental signal as a function of an air flow rate signal through the internal combustion engine, wherein the second signal is formed as a function of the fundamental signal and at least one correction signal.

* * * * *